US006036114A

United States Patent [19]

Shih

[11] Patent Number: 6,036,114

[45] Date of Patent: Mar. 14, 2000

[54] DEVICE FOR CONTROLLING PRESSURE OF PAINT CONTAINER FOR USE IN CONJUNCTION WITH PAINT SPRAY GUN

[75] Inventor: Hsien Chun Shih, Changhua, Taiwan

[73] Assignee: Ding Rong Enterprise Co., Ltd., Taiwan

[21] Appl. No.: 09/227,548

[22] Filed: Jan. 11, 1999

[51] Int. Cl.[7] .............................. A61M 11/02; B05B 7/30

[52] U.S. Cl. .......................... 239/364; 239/347; 239/348; 239/365

[58] Field of Search .................................... 239/346, 347, 239/348, 364, 365, 373

[56] References Cited

U.S. PATENT DOCUMENTS 4,174,070 11/1979 Lau et al. ............................ 239/347 X
4,174,071 11/1979 Lau et al. ................................ 239/348
5,119,992 6/1992 Grime .................................... 239/364
5,236,128 8/1993 Morita et al. ....................... 239/365 X

*Primary Examiner*—Andres Kashnikow
*Assistant Examiner*—Robin O. Evans
*Attorney, Agent, or Firm*—Smith, Gambrell & Russell, LLP

[57] ABSTRACT

A pressure controlling device of a paint container for use in conjunction with a paint spray gun is composed of a pressure stabilizing plug capable of regulating the air discharge in accordance with the magnitude of the air pressure that is admitted to the paint container. The device is further composed of an air valve piece capable of displacing to control the entry of an appropriate amount of air into the paint container so as to keep the air pressure of the paint container constant. The device is provided with an adjustment nut for adjusting the elastic force of the pressure stabilizing plug in accordance with the desired thickness of a coating.

1 Claim, 5 Drawing Sheets

DEVICE FOR CONTROLLING PRESSURE OF PAINT CONTAINER FOR USE IN CONJUNCTION WITH PAINT SPRAY GUN

FIELD OF THE INVENTION

The present invention relates generally to an auxiliary painting implement, and more particularly to an air pressure controlling device of a paint container for use in conjunction with a paint spray gun.

BACKGROUND OF THE INVENTION

The paint contained in the conventional paint container is drawn out by siphonage into a paint gun. In order to effect the siphonage, a considerable air current pressure is called for at the expense of the mechanical power. In light of the presence of excessive air current pressure, the paint is prone to be shot out by the paint spray gun in an excessive amount to result in the waste of the paint as well as the pollution of air by the paint spray. In addition, the coating so formed is often uneven in thickness.

SUMMARY OF THE INVENTION

It is therefore the primary objective of the present invention to provide a pressure controlling device to eliminate the drawbacks of the prior art described above.

The objective of the present invention is achieved by the pressure controlling device consisting of a pressure stabilizing plug capable of regulating the air current discharge in accordance with the magnitude of the air pressure that is admitted to the paint container. The device further consist of an air valve piece capable of displacing to control the entry of an appropriate amount of air into the paint container so as to keep the air pressure inside the paint container constant. The device is provided with an adjustment nut for adjusting the elastic force of the pressure stabilizing plug in accordance with the desired thickness of a coating.

The objective, features and functions of the present invention will be more readily understood upon a thoughtful deliberation of the following detailed description of a preferred embodiment of the present invention with reference to the drawings provided herewith.

DETAILED DESCRIPTION OF THE EMBODIMENT

Figure 1A:
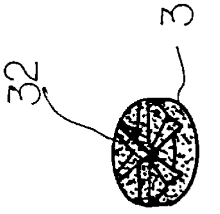
FIG. 1A shows a schematic view of the structure of the bottom of an air valve piece of the preferred embodiment of the present invention.
Figure 1:
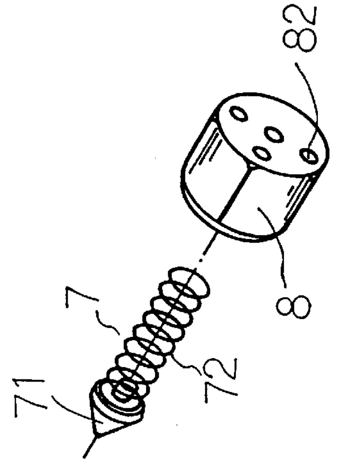
FIG. 1 shows an exploded view of the preferred embodiment of the present invention.
Figure 1:
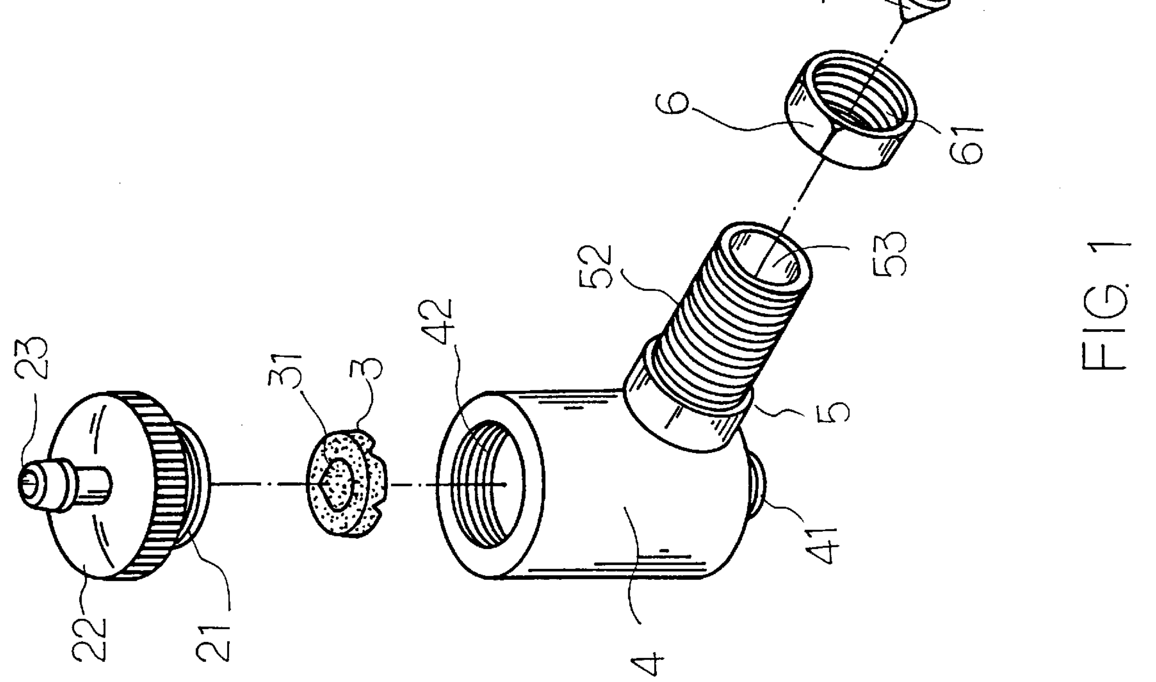

As shown in all drawings provided herewith, an air pressure controlling device embodied in the present invention is intended for use in conjunction with a paint spray gun which is mounted on a paint container 1. The device of the present invention is composed of an air admission connector 2, an air valve piece 3, an air guiding main body 4, an adjustment nut 6, a pressure stabilizing plug 7, and an air discharge nut 8.

The air guiding main body 4 is provided in the bottom thereof with a threaded protrusion 41 of a hollow construction, and in the upper portion thereof with an inner threaded hole 42 in communication with an air admission duct 43 extending through the threaded protrusion 41. The main body 4 has an air discharging head 5 extending therefrom and having outer threads 52, a slot 53 of an appropriate depth, and a through hole 54 in communication with the air admission duct 43.

The air admission connector 2 is provided in the bottom thereof with an outer threaded portion 21 which is engaged with the inner threaded hole 42 of the main body 4. The air admission connector 2 is provided in the top thereof with a connection head 22 having a through hole 23. The connection head 22 is connected with one end of a pliable tube S which is connected at other end thereof with the paint spray gun mounted on the paint container 1.

The air valve piece 3 is disposed in the inner threaded hole 42 of the main body 4 and is provided in the upper surface thereof with a tapered portion 31 and in the underside thereof with a plurality of slots 32 which are arranged in a radiate manner.

The adjustment nut 6 has inner threads 61 which are engaged with the outer threads 52 of the air discharging head 5.

The pressure stabilizing plug 7 is composed of a plug block 71 and a spring 72 fastened at one end thereof with the plug block. The plug block 71 is dimensioned to obstruct the through hole 54 of the air discharging head 5.

The air discharge nut 8 has inner threads 81 which are engaged with the outer threads 52 of the air discharging head 5. The air discharge nut 8 is provided with a plurality of air discharging holes 82.

Figure 2:
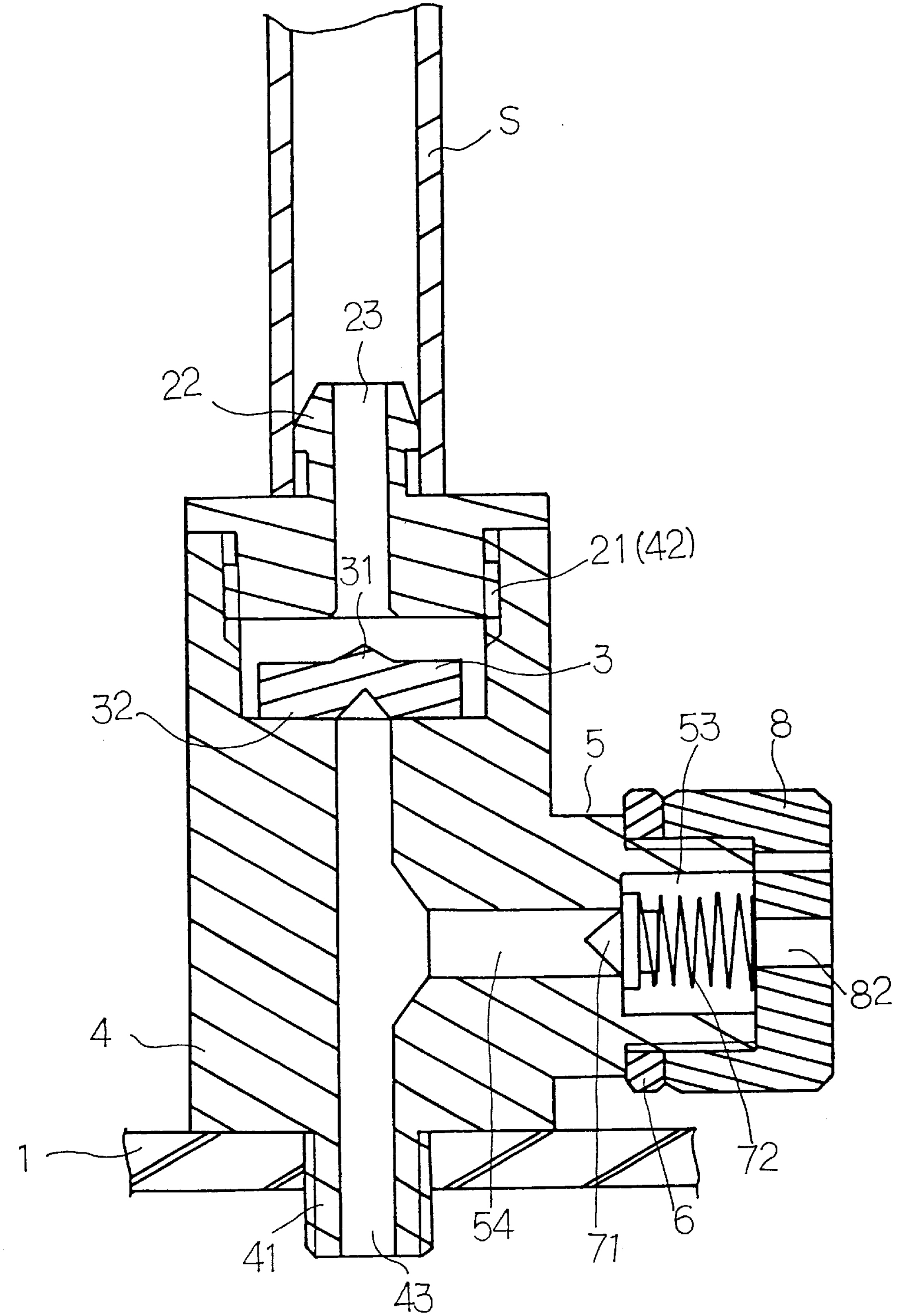
FIG. 2 shows a sectional view of the preferred embodiment of the present invention in combination.
Figure 2A:
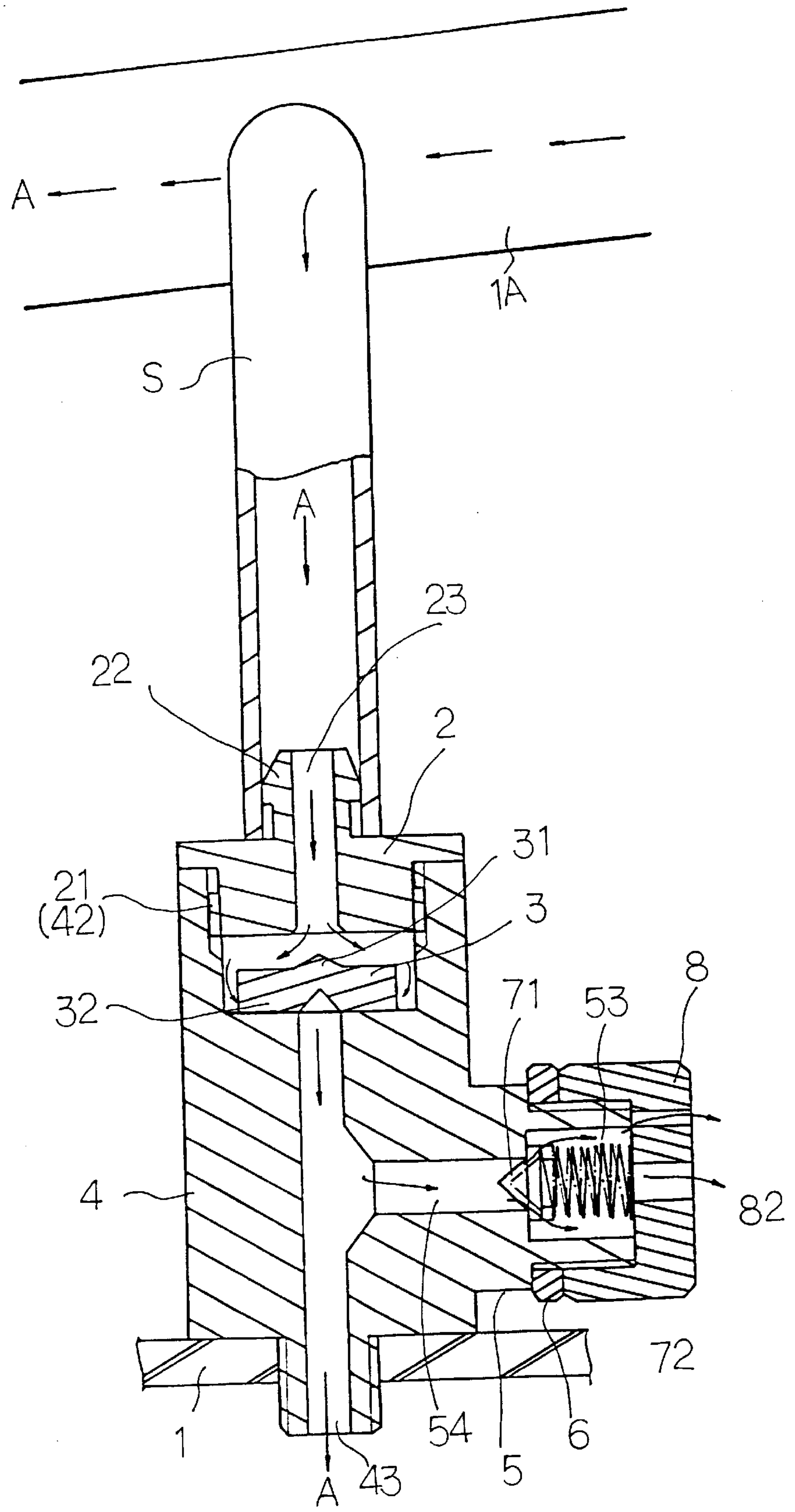
FIG. 2A shows a schematic sectional view of the preferred embodiment of the present invention in use.
Figure 2B:
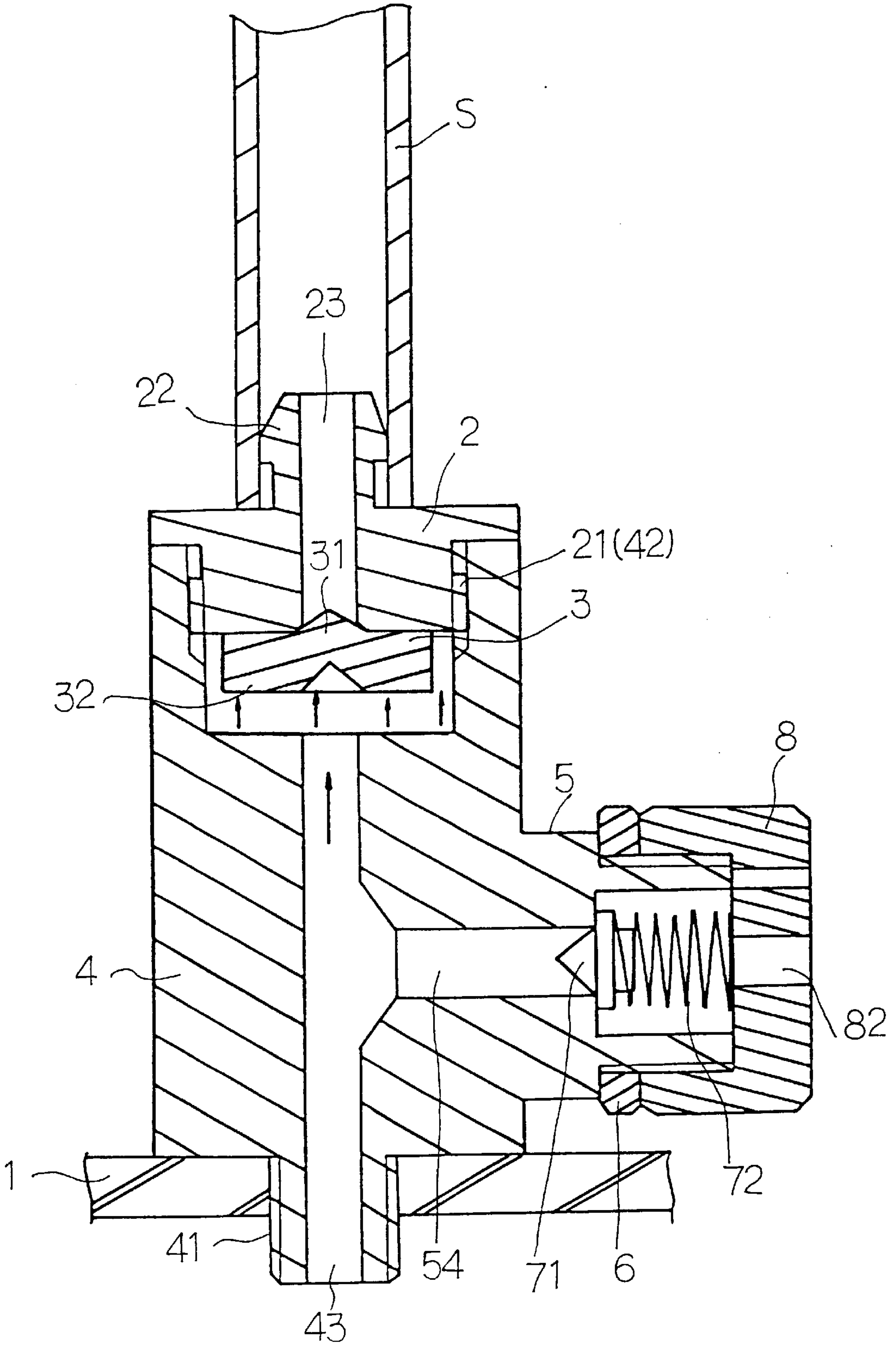
FIG. 2B shows a schematic view of the present invention in the state of interruption of air admission.
Figure 3:
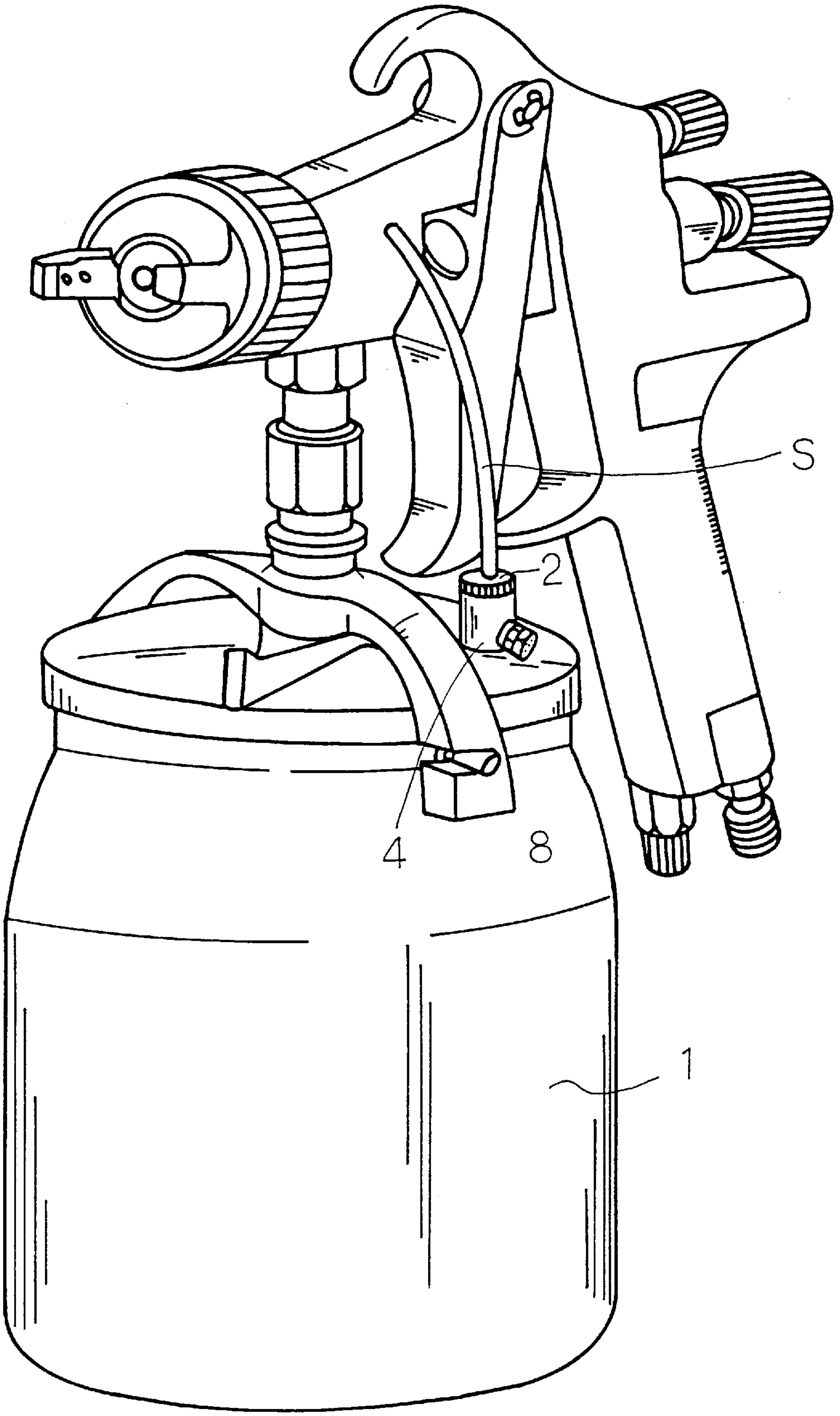
FIG. 3 shows a schematic view of the present invention in conjunction with a paint container and a paint spray gun.

As shown in FIG. 2, when the device of the present invention is not in operation, the air valve piece 3 is located at the bottom of the inner threaded hole 42. The threaded protrusion 41 of the main body 4 is engaged with the paint container 1. The connection head 22 of the air admission connector 2 is connected with one end of the pliable tube S which is in turn connected at other end thereof with an air duct 1A of the paint spray gun. The air current A in the air duct 1A of the paint spray gun is thus guided into the air admission connector 2. The air current A is converged in the air admission duct 43 via the tapered portion 31 and the radiate slots 32 of the air valve piece 3. The air current A is introduced into the paint container 1 via the air admission duct 43, as shows in FIG. 2A. When the air current A has reached a saturation point, the air pressure inside the through hole 54 is greater than the elastic force of the spring 72 of the pressure stabilizing plug 7, thereby causing the plug block 71 of the pressure stabilizing plug 7 to move aside from the through hole 54 so as to allow the passage of the air current A, which is then discharged into the atmospheric air via the air discharging holes 82 of the air discharging nut 8. As a result, air pressure inside the paint container 1 is kept constant. When the painting operation is interrupted or terminated, the air pressure of the paint container 1 forces the air valve piece 3 to ascend such that the tapered portion 31 of the air valve piece 3 obstructs the through holes 23 of the connection head 22 of the air admission connector 2, so as to prevent the escape of air of the paint container 1, as illustrated in FIG. 2B.

The spring 72 is substantially compressed when the adjustment nut 6 is located at the most inner end of the outer threads 52 of the air discharging head 5. The spring 72 is thus provided with a greater recovery force. Only a small quantity of air current A can pass the plug 7. The residual high air pressure of the paint container 1 can be set, as shown in FIG. 2A. When the adjustment nut 6 is moved toward the outer end of the outer threads 52 of the air discharging head 5, the spring 72 is less compressed such that the spring 72 is provided with a less recovery force. A greater quantity of air current can pass the plug 7. The residual low air pressure of the paint container 1 can be set, as shown in FIG. 2B. As a result, the device of the present invention enables the worker to adjust the air pressure in accordance with the desired thickness of a coating.

The embodiment of the present invention described above is to be deemed in all respects as being merely illustrative and not restrictive. Accordingly, the present invention may be embodied in other specific forms without deviating from the spirit thereof. The present invention is therefore to be limited only by the scope of the following appended claim.

What is claimed is:

1. A device for controlling air pressure of a paint container for use in conjunction with a paint spray gun, said device comprising:

an air guiding main body provided at a bottom thereof with a threaded protrusion, and in an upper portion thereof with an inner threaded hole in communication with an air admission duct extending through said threaded protrusion, said main body having an air discharging head extending therefrom and having outer threads, a slot of a predetermined depth, and a through hole in communication with said air admission duct;

an air admission connector provided in a bottom thereof with an outer threaded portion which is engaged with said inner threaded hole of said main body, and in a top thereof with a connection head having a through hole and connected with one end of a pliable tube which is in turn connected at other end thereof with the paint spray gun mounted on the paint container;

an air valve piece disposed in said inner threaded hole of said main body and provided in an upper surface thereof with a tapered portion and in an underside thereof with a plurality of slots arranged in a radiate manner;

an adjustment nut having inner threads which are engaged with said outer threads of said air discharging head;

a pressure stabilizing plug formed of a plug block and a spring fastened at one end thereof with said plug block, said plug block so dimensioned to obstruct said through hole of said air discharging head; and an air discharge nut having inner threads which are engaged with said outer threads of said air discharging head, said air discharge nut further having a plurality of air discharging holes;

said threaded protrusion of said main body being connected with the paint container such that said connection head of said air admission connector is connected with one end of the pliable tube which is in turn connected at other end thereof with an air duct of the paint spray gun, and that air current in the air duct of the paint spray gun is guided into said air admission connector and then converged in said air admission duct of said main body via said tapered portion of said air valve piece and said radiate slots of said air valve piece, and further that the air current is introduced into the paint container via said air admission duct of said main body;

air pressure inside said through hole of said air discharging head of said main body being greater than an elastic force of said spring at the time when the air current has reached a saturation point, thereby causing said plug block of said pressure stabilizing plug to move aside from said through hole of said air discharging head of said main body so as to allow the passage of the air current which is then discharged into the atmospheric air via said air discharging holes of said air discharge nut;

said air valve piece capable of being force by the air pressure of the paint container to ascend at the time when the paint spray gun is not in operation, such that said tapered portion of said air valve piece obstructs said through hole of said connection head of said air admission connector so as to prevent the escape of air of the paint container.

* * * * *